United States Patent
House et al.

[11] Patent Number: 6,048,484
[45] Date of Patent: *Apr. 11, 2000

[54] PROCESS FOR FORMING A SEAMLESS TUBE OF EXPANDED PTFE FROM A SHEET OF EXPANDED PTFE

[75] Inventors: Wayne D. House, Flagstaff; Kenneth W. Moll, Camp Verde; Stanislaw L. Zukowski, Flagstaff, all of Ariz.

[73] Assignee: W. L. Gore & Associates, Inc., Newark, Del.

[*] Notice: This patent issued on a continued prosecution application filed under 37 CFR 1.53(d), and is subject to the twenty year patent term provisions of 35 U.S.C. 154(a)(2).

[21] Appl. No.: 08/749,478

[22] Filed: Nov. 1, 1996

Related U.S. Application Data

[62] Division of application No. 08/412,840, Mar. 29, 1995, Pat. No. 5,620,763, which is a continuation of application No. 08/108,960, Aug. 18, 1993, abandoned.

[51] Int. Cl.[7] .................................................... B29C 51/04
[52] U.S. Cl. ................................... 264/322; 264/331.14
[58] Field of Search ................................ 264/322, 320, 264/321, 331.14, 554

[56] References Cited

U.S. PATENT DOCUMENTS

| | | | |
|---|---|---|---|
| 2,781,552 | 2/1957 | Gray | 264/331.14 |
| 3,953,566 | 4/1976 | Gore | 264/288 |
| 4,187,390 | 2/1980 | Gore | 174/102 R |
| 4,203,938 | 5/1980 | Burnett et al. | 264/331.14 |
| 4,419,320 | 12/1983 | Perkins et al. | 264/322 |
| 4,482,516 | 11/1984 | Bowman et al. | 264/127 |
| 4,563,325 | 1/1986 | Coffman | 264/322 |
| 4,877,661 | 10/1989 | House et al. | 428/34.9 |
| 4,957,669 | 9/1990 | Primm | 264/331.14 |
| 5,026,513 | 6/1991 | House et al. | 264/127 |
| 5,466,509 | 11/1995 | Kowligi et al. | 428/141 |
| 5,620,763 | 4/1997 | House et al. | 428/36.9 |

FOREIGN PATENT DOCUMENTS

| | | |
|---|---|---|
| 0313263 | 4/1989 | European Pat. Off. . |
| 55-36492 | of 1980 | Japan . |
| 2033234 | 5/1980 | United Kingdom . |
| 9113648 | 9/1991 | WIPO . |

*Primary Examiner*—Jill L. Heitbrink
*Assistant Examiner*—Mark Eashoo
*Attorney, Agent, or Firm*—Wayne D House

[57] ABSTRACT

A method of making a seamless, thinwall tube of porous polytetrafluoroethylene. The method involves the use of corresponding male and female dies to deform a precursor sheet of porous PTFE which has been restrained about its perimeter. Preferably the porous PTFE sheet is heated to a temperature of less than the crystalline melt temperature during the tube-forming process. The precursor material is preferably a sheet of porous expanded PTFE and more preferably a multiaxially expanded sheet. This precursor material may optionally have been previously exposed to heat above the melt temperature of PTFE. The inventive tube is as thin or thinner than the precursor sheet.

14 Claims, 3 Drawing Sheets

PROCESS FOR FORMING A SEAMLESS TUBE OF EXPANDED PTFE FROM A SHEET OF EXPANDED PTFE

This application is a division, of application Ser. No. 08/412,840, filed Mar. 29, 1995 now U.S. Pat. No. 5,620,763, which is a continuation of application Ser. No. 08/108,960 filed Aug. 18, 1993 now abandoned.

FIELD OF THE INVENTION

This invention relates to the field of porous expanded polytetrafluoroethylene materials of seamless, tubular form.

BACKGROUND OF THE INVENTION

Porous expanded polytetrafluoroethylene (hereinafter PTFE) materials are made as taught originally by U.S. Pat. Nos. 3,953,566 and 4,187,390 to Gore. These patents teach the manufacture of seamless, tubular forms of porous expanded PTFE by a process comprising extruding a preform of PTFE resin and a lubricant through a tubular extruder barrel having a male form aligned with the longitudinal axis of the tubular barrel, thereby creating a tubular extrudate, removing the lubricant from the tubular extrudate, expanding the tubular extrudate by stretching in a direction parallel to the longitudinal axis of the tubular extrudate at a temperature less than the crystalline melt point of PTFE, thereby forming a tube of porous expanded PTFE having a microstructure of nodes interconnected by fibrils. These porous expanded PTFE tubes have found application in the field of implantable vascular grafts. These are presently sold as GORE-TEX® Vascular Grafts (W. L. Gore & Associates, Inc., Flagstaff, Ariz.) and are in the form of tubes of porous expanded PTFE with an exterior reinforcement of a helical wrap of thin, porous expanded PTFE film to provide the grafts with increased hoop strength.

Present commercially available seamless tubes of porous expanded PTFE made by a process including extrusion typically have wall thicknesses of about 0.31 mm or greater. The present limitation on thinner walls is due to the extrusion and subsequent expansion process which is unable to produce these thinner walls with adequate concentricity and uniformity.

It is speculated that thinner-walled seamless tubes would be useful in certain vascular graft applications wherein the tube may serve as a replacement for segments of blood vessels. These include tubes of inside diameter less than about 2 mm. Thin-walled seamless tubes of even larger inside diameter may be useful as intraluminal vascular grafts and as coverings for intraluminal stents, both of which are used as luminal linings of body conduits.

SUMMARY OF THE INVENTION

The present invention is a seamless tube of porous PTFE having a wall thickness of less than about 0.20 mm, and a method of making the seamless tube. Porous PTFE is herein defined as PTFE containing void spaces within the bulk volume of the porous PTFE shape, and having a bulk density of less than about 2.0 g/cc. Solid, non-porous PTFE has a bulk density of about 2.2 g/cc. The presence of void spaces may be identified by visually examining surfaces of the PTFE shape which may be surfaces of cross sections of the shape. This examination may require the aid of microscopy.

By seamless tube is meant a tube without any seam that extends from the exterior surface through to the luminal surface. Tubes formed by rolling a sheet into a tubular shape incorporate such seams and are therefore not considered to be seamless. Tubes of the present invention may, however, have additional, seamed layers added to either the exterior or luminal surfaces as long as no seam extends from the exterior surface through to the luminal surface.

The method of making the seamless tube comprises selecting a precursor sheet of porous PTFE, clamping around the perimeter of the sheet to restrain the sheet and forming a portion of the sheet into a tubular shape by forcing a male form against the sheet thereby forcing a portion of the sheet into a female form, wherein the longitudinal axes of the male form and female form are substantially perpendicular to the plane of the sheet. The formed tubular shape may then be cut free from the remaining flat portion of the sheet.

The clamped sheet of porous PTFE is preferably heated prior to the forming step. Less force is required for forming with increasing application of heat.

It is also preferred that the precursor sheet of porous PTFE be of less than about 0.20 mm thickness. It is further preferred that the precursor sheet of porous PTFE has not been subjected to heat in excess of the crystalline melt temperature of PTFE.

Preferred precursor sheet materials are sheets of porous expanded PTFE having a microstructure of nodes interconnected by fibrils, made as taught by U.S. Pat. Nos. 3,953,566 and 4,187,390. It is still further preferred that the precursor sheet of porous expanded PTFE have a symmetrical microstructure of biaxially or multiaxially-oriented fibrils. These sheets having symmetrical microstructures can be expected to yield tubes of relatively uniform microstructure when formed by the method of the present invention. Sheets with symmetrical microstructures have fibrils oriented in at least two directions which are substantially perpendicular to each other and wherein the fibrils in the at least two directions are of approximately the same lengths. Microstructures having a substantial majority of fibrils oriented in only two directions that are substantially perpendicular to each other are considered to have biaxially-oriented fibrils. Another preferred symmetrical microstructure for the precursor sheet material has multiaxially-oriented fibrils, that is, fibrils oriented in virtually all directions within the plane of the sheet, the fibrils emanating from the nodes in all directions similar to the way spokes emanate from a wheel hub. The fibrils of these various directions should also be of approximately equal lengths. Porous expanded PTFE sheet materials having symmetrical microstructures are made by biaxial expansion processes taught by U.S. Pat. Nos. 3,953,566; 4,187,390 and 4,482,516.

Seamless tubes of the present invention may be provided with an exterior helical wrap of thin porous expanded PTFE film if a tube of increased hoop strength is desired. Additionally, seamless tubes of the present invention may be provided with rapid recovery properties as taught by U.S. Pat. Nos. 4,877,661 and 5,026,513. These patents are herein incorporated by reference.

DETAILED DESCRIPTION OF THE INVENTION

Figure 1:
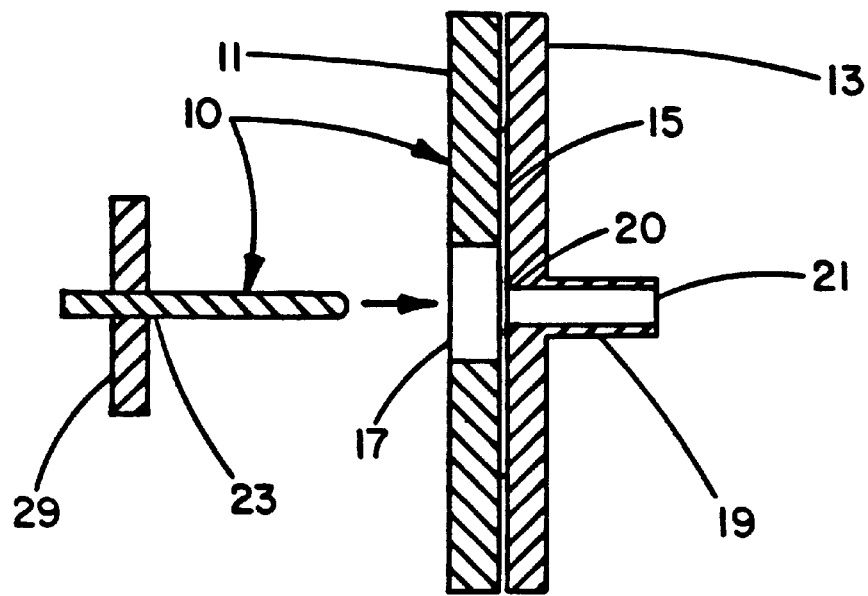
FIG. 1 describes a cross section of a clamping fixture incorporating male and female forms, useful for forming the tube of the present invention.

FIG. 1 describes a cross section of a fixture 10 useful for forming the seamless tube of the present invention. Clamping plates 11 and 13 are clamped around the perimeter of a flat sheet 15 of porous expanded PTFE. Clamping plate 11 is provided with an access hole 17 to allow male form 23 to be forced against the flat sheet 15. The male form 23 may optionally be provided with a stop 21 to control the length of the formed seamless tube. Clamping plate 13 is provided with a female form 19 having an open end 21 opposite the access hole 17 in plate 11. The other end of the female form 19 adjacent to the flat sheet 20 should be provided with a radiused entrance 20. Access hole 17 should be of substantially larger diameter than the male form 23 in order to allow for enough material from flat sheet 15 to be deformed into the desired tubular shape. For example, access hole 17 may be more than three times the diameter of male form 23. Generally, the larger the access hole 17 and the larger the area of flat sheet 15 within the clamped perimeter, the more material is available to be drawn into the tubular shape, thereby allowing for the longer tubular shapes to be formed.

The inside diameter of the female form 19 should allow clearance for the thickness of the flat sheet 15 around the male form 23 during the forming process. Put another way, the inside diameter of the female form 19 should be equal to at least the sum of the diameter of the male form 23 and twice the thickness of the flat sheet 15. If too little clearance is provided, smearing of the inner or outer surfaces of the tube microstructure may occur, thereby substantially reducing the porosity of the resulting tube. Both the male form 23 and the female form 19 may be provided with slight amounts of taper to allow easier release of these components after the forming process is complete. These tapers are such that the open end 21 of female form 19 and corresponding end of male form 23 are provided with the smaller diameter of the taper. The amount of taper may be quite small, for example, a diametrical end to end difference of 0.1 mm may be useful.

Figure 2:
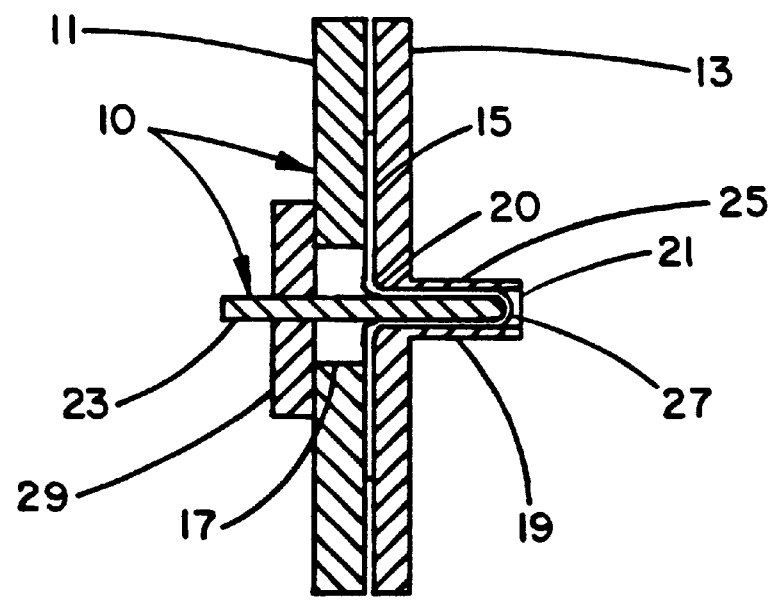
FIG. 2 describes a cross section of the clamping fixture of FIG. 2 as used during the forming process.

FIG. 2 describes a cross section of the forming fixture 10 after completion of the forming step. A portion of the flat sheet 15 has been formed between the male form 23 and female form 19 to create the seamless, thin-wall tube portion 25. After the forming step is complete the male form 23 is removed and the clamping plates 11 and 13 are separated, thereby releasing the flat sheet 15 and the seamless, thin-wall tube portion 25. The seamless, thin-wall tube portion 25 may then be cut free from the remainder of the flat sheet 15 using a sharp blade to accomplish the cutting. Tip portion 27 may be retained with the seamless, thin-wall tube portion 25 if a blind tube is desired. Alternatively, if a tube with both ends open is desired, then the tip portion 27 may also be cut away.

It is preferred that the flat sheet 15 be heated during the forming step. In order to accomplish this, the forming fixture 10 should be secured into place in an oven operating at the desired temperature. After adequate heating, the forming force may be applied to the flat sheet 15 from outside of the oven chamber by the use of a male form 23 of length adequate to extend outside of the oven chamber through an opening provided in the oven wall.

Figure 3A:
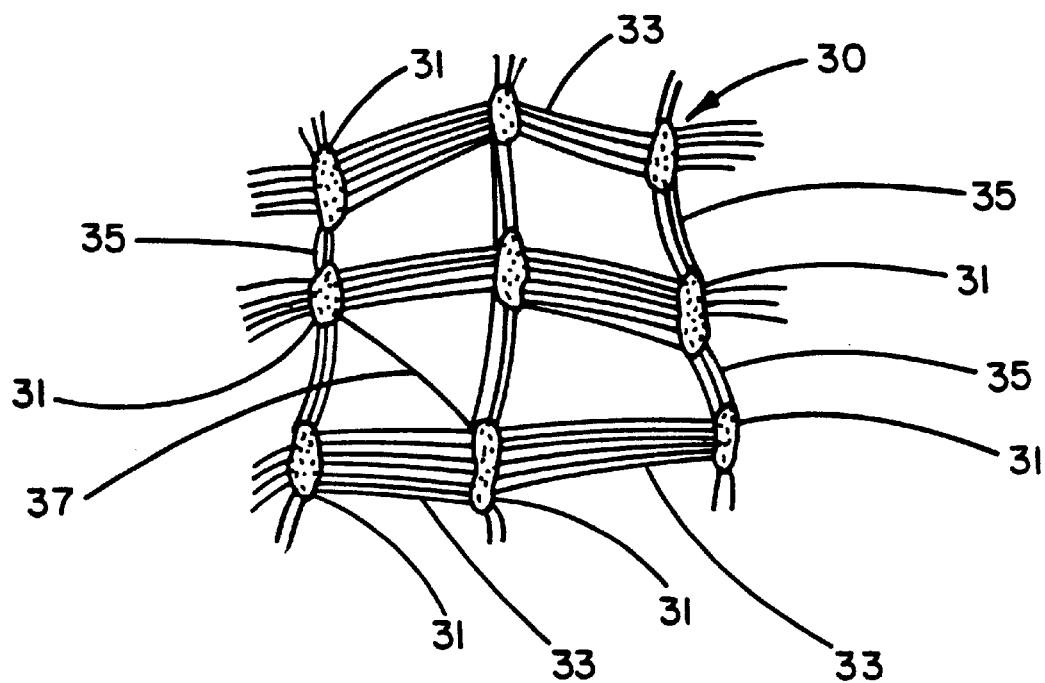
FIG. 3A is an enlarged schematic representation of a porous expanded PTFE precursor sheet material having a preferred symmetrical microstructure with biaxially-oriented fibrils.
Figure 3B:
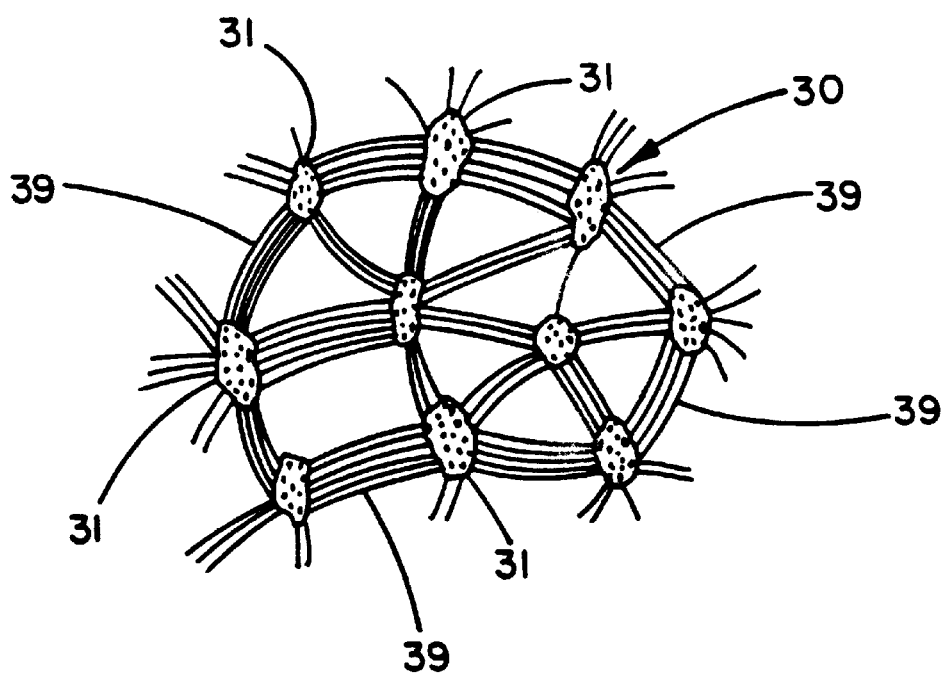
FIG. 3B is an enlarged schematic representation of a porous expanded PTFE precursor sheet material having a preferred symmetrical microstructure with multiaxially-oriented fibrils.

FIGS. 3A and 3B describe enlarged schematic representations of symmetrical microstructures of porous expanded PTFE precursor sheet materials that are the preferred precursor sheet materials for making the present invention. These symmetrical microstructures have nodes interconnected by fibrils wherein the fibrils are oriented in at least two directions which are substantially perpendicular to each other. FIG. 3A describes a symmetrical microstructure of nodes 31 and fibrils 33 and 35 wherein the fibrils 33 and 35 are biaxially-oriented fibrils which are oriented in two different directions that are substantially perpendicular to each other. Those microstructures may contain some fibrils 37 which are not oriented in the two different directions. FIG. 3B describes another symmetrical microstructure wherein the fibrils 39 are multiaxially-oriented fibrils oriented in virtually all directions within the plane of the sheet material.

Figure 4:
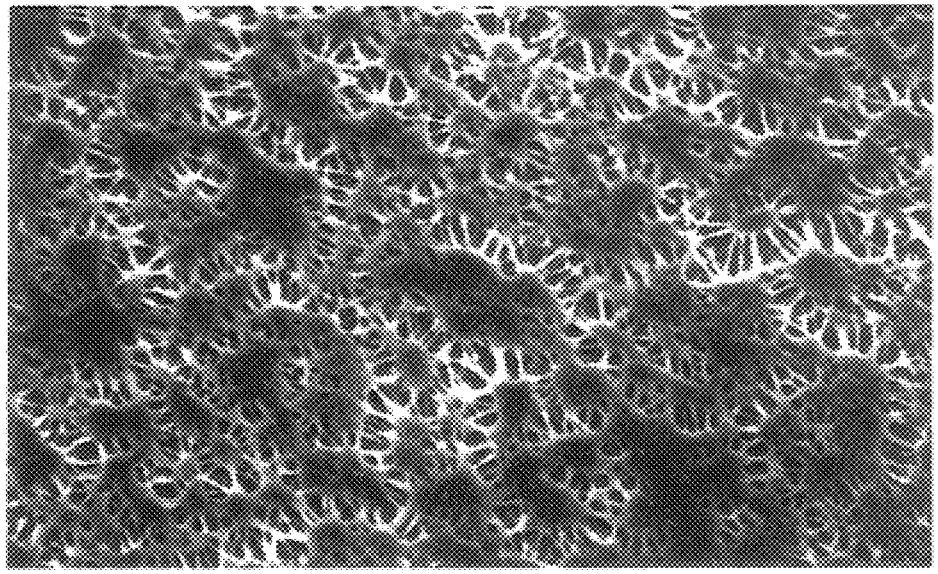
FIG. 4 shows a scanning electron photomicrograph (×2000 magnification) of the microstructure of nodes interconnected by fibrils of a precursor sheet of porous expanded PTFE used to form a seamless tube of the present invention.

FIG. 4 shows a scanning electron photomicrograph of the microstructure of nodes interconnected by fibrils of a precursor sheet of porous expanded PTFE used to form a seamless tube of the present invention. This particular sheet is 0.1 mm thick GORE-TEX® Surgical Membrane (W. L. Gore and Associates, Inc., Flagstaff, Ariz.). This is a sheet material that has been subjected to heat in excess of the crystalline melt temperature of PTFE. It has a microstructure of multiaxially-oriented fibrils wherein the fibrils are oriented in virtually all directions within the plane of the sheet, the fibrils emanating radially outward from each node in the fashion of spokes emanating from the hub of a wheel. Precursor sheet materials having symmetrical microstructures are preferred in order to produce a tube of relatively uniform microstructure.

Figure 5:
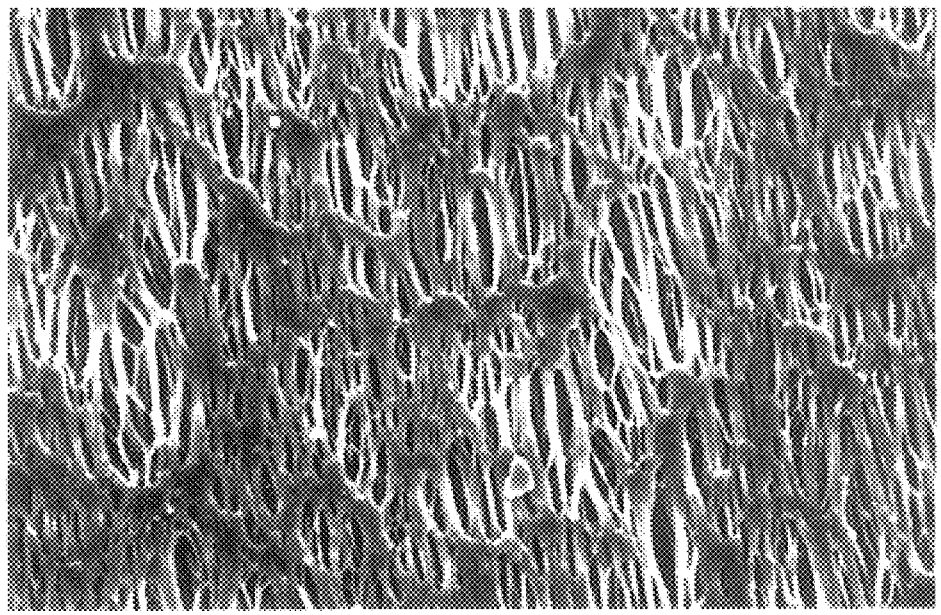
FIG. 5 shows a scanning electron photomicrograph (×2000 magnification) of the luminal surface of a tube of the present invention.

FIG. 5 describes a scanning electron photomicrograph (×2000 magnification) of the luminal surface of a tube of the present invention that was made from the precursor sheet material described by FIG. 4. The surface shown has a microstructure of nodes interconnected by fibrils wherein the fibrils are substantially oriented in a direction parallel to the longitudinal axis of the tube and parallel to the direction of the applied forming force. The tube had a relatively uniform wall thickness of about 0.07 mm, an inside diameter of about 8 mm, and a length of about 3 cm.

This example tube was made by clamping a sheet of 0.1 mm thick GORE-TEX® Surgical Membrane into a fixture 10 similar to that described by FIGS. 1 and 2. This fixture had a 24 mm diameter access hole 17 and used a female form 19 of 9 mm inside diameter and 2.6 cm length. The male form 23 was of 8.0 mm diameter and 150 cm length. This assembly was secured into place within a convection air oven set at about 300° C. so that the male form 23 extended through an opening in the oven wall. After 20 minutes heating time within the oven, about 2.5 kg force was applied to male form 23 at a rate of about 1 mm/sec. The fixture 10 was then removed from the oven and allowed to cool, after which it was disassembled to free the flat sheet 15 and seamless, thin-wall tube portion 25. The seamless, thin-wall tube portion 25 was cut free from the flat sheet 15 using a scalpel blade. The tip portion 27 of the seamless, thin-wall tube portion 25 was also cut off. The wall thickness of the resulting tube was measured by cutting lengthwise through a portion of the tube wall and measuring the tube wall thickness adjacent to the cut using a Mitutoyo snap gauge Model No. 2804-10 having a part no. 7300 frame. A sample of the tube wall was then cut away with a scalpel blade to be photographed for the scanning electron photomicrograph of FIG. 5.

While this example involved the use of a precursor sheet material that had been exposed to temperatures in excess of the crystalline melt temperature of PTFE, it is preferred that porous PTFE sheet materials that have not been subjected to such temperatures be used as precursor materials in that they are more easily formed into the desired shape. Tubes made from such sheet materials may be subsequently heated by physically restraining them in the direction of the longitudinal axis of the tube and then heating them above the crystalline melt temperature of PTFE.

A second example was made from a porous expanded PTFE sheet material having biaxially-oriented fibrils wherein most of the fibrils were substantially oriented in a single direction. This material also possessed shorter fibrils oriented in a direction substantially perpendicular to the longer fibrils of the first direction. The sheet material used was GORE-TEX® Filtration Membrane, part no. 10382 NA (W. L. Gore & Associates, Inc., Elkton, Md.). Two layers of this 0.05 mm thick membrane were stacked one above the other with a 0.013 mm thick, non-porous layer of fluorinated ethylene propylene (hereinafter FEP) between the two expanded PTFE layers. The two porous expanded PTFE layers were oriented 90° apart so that the longer fibrils of one layer were oriented in a direction substantially perpendicular to the longer fibrils of the second layer. The resulting three layer sandwich was clamped into the fixture described by FIG. 1 and placed into an oven set at 315° C. with the flat sheet 15 oriented horizontally and the male form 23 oriented vertically and located above the flat sheet 15. After 30 minutes, the sandwich was formed into a tube in the same fashion described for the previous example. Forming was accomplished with a force of about 0.6 kg at a rate of about 2 mm/second. The force was applied simply by placing a weight on the male form 23 and stop 29; the combined weight of the male form 23, stop 29 and weight was 0.6 kg. The resulting tube was impermeable due to the presence of the non-porous FEP layer and was of about 3 cm length with a wall thickness of about 0.05 mm.

We claim:

1. A method for making a seamless tube of porous expanded polytetrafluoroethylene having a microstructure of nodes interconnected by fibrils comprising selecting a sheet of porous expanded polytetrafluoroethylene having a perimeter and having a microstructure of nodes interconnected by fibrils, clamping around the perimeter of the sheet to restrain the sheet, and forming a portion of the sheet into a tubular shape by forcing a male form against the sheet thereby forcing a portion of the sheet into a female form, wherein the longitudinal axes of the male and female forms are substantially perpendicular to the sheet.

2. A method according to claim 1 wherein the sheet of porous expanded polytetrafluoroethylene is heated to at least about 290° C. prior to forming a portion of the sheet into a tubular shape.

3. A method according to claim 1 wherein said tube has a wall thickness of less than about 0.20 mm.

4. A method according to claim 1 wherein said tube has a wall thickness of less than about 0.15 mm.

5. A method according to claim 1 wherein said tube has a wall thickness of less than about 0.10 mm.

6. A method according to claim 1 wherein said tube has a wall thickness of less than about 0.06 mm.

7. A method according to claim 1 wherein the tube has a wall thickness of less than about 0.08 mm.

8. A method according to claim 1 wherein the sheet has been heated to a temperature greater than the crystalline melt temperature of PTFE prior to forming the sheet into a tubular shape.

9. A method according to claim 8 wherein the sheet has a wall thickness and tube has a wall thickness of less than the wall thickness of the sheet.

10. A method according to claim 8 wherein the tube has a wall thickness of less than about 0.08 mm.

11. A method according to claim 1 wherein said sheet of porous expanded polytetrafluoroethylene has multiaxially-oriented fibrils.

12. A method according to claim 11 wherein said seamless tube of porous expanded polytetrafluoroethylene has a longitudinal axis and wherein the fibrils of the microstructure of the seamless tube are substantially oriented in a direction parallel to the longitudinal axis.

13. A method according to claim 1 wherein said sheet of porous expanded polytetrafluoroethylene has biaxially-oriented fibrils.

14. A method according to claim 11 wherein said seamless tube of porous expanded polytetrafluoroethylene has a longitudinal axis and wherein the fibrils of the microstructure of the seamless tube are substantially oriented in a direction parallel to the longitudinal axis.

* * * * *